(12) United States Patent
Dargazanli et al.

(10) Patent No.: US 7,951,821 B2
(45) Date of Patent: May 31, 2011

(54) N-[PHENYL(PIPERIDIN-2-YL)METHYL] BENZAMIDE DERIVATIVES, PREPARATION THEREOF, AND USE THEREOF IN THERAPY

(75) Inventors: Gihad Dargazanli, Cachan (FR); Genevieve Estenne-Bouhtou, Chevilly-Larue (FR); Benoit Marabout, Massy (FR); Pierre Roger, Montigny-le-Bretonneux (FR); Mireille Sevrin, Paris (FR)

(73) Assignee: sanofi-aventis, Paris (FR)

( * ) Notice: Subject to any disclaimer, the term of this patent is extended or adjusted under 35 U.S.C. 154(b) by 1108 days.

(21) Appl. No.: 11/680,782

(22) Filed: Mar. 1, 2007

(65) Prior Publication Data
US 2007/0155789 A1 Jul. 5, 2007

Related U.S. Application Data

(63) Continuation of application No. 11/045,247, filed on Jan. 28, 2005, now Pat. No. 7,205,319, which is a continuation of application No. PCT/FR03/02356, filed on Jul. 25, 2003.

(30) Foreign Application Priority Data

Jul. 29, 2002 (FR) ..................................... 02 09588

(51) Int. Cl.
*A61K 31/445* (2006.01)
(52) U.S. Cl. ...................... 514/317; 514/235.5; 514/331; 544/126; 546/186; 546/207; 546/234; 546/247
(58) Field of Classification Search .................. 514/331, 514/235.5, 317; 544/126; 546/186, 207, 546/234, 247
See application file for complete search history.

(56) References Cited

U.S. PATENT DOCUMENTS

| | | | |
|---|---|---|---|
| 2,928,835 A | 3/1960 | Jacob et al. | |
| 3,336,300 A | 8/1967 | Santilli et al. | |
| 3,801,636 A | 4/1974 | Horrom | |
| 5,254,569 A | 10/1993 | Cheeseman et al. | |
| 5,364,868 A | 11/1994 | Englert et al. | |
| 6,894,054 B2 * | 5/2005 | Laborde et al. | 514/255.05 |
| 7,226,917 B2 | 6/2007 | Dargazanli et al. | |
| 7,288,656 B2 | 10/2007 | Dargazanli et al. | |
| 7,300,946 B2 | 11/2007 | Ding et al. | |
| 7,326,722 B2 | 2/2008 | Dargazanli et al. | |
| 7,326,732 B2 | 2/2008 | Oxford et al. | |
| 7,335,670 B2 | 2/2008 | Dargazanli et al. | |
| 7,507,824 B2 * | 3/2009 | Gibson et al. | 546/15 |
| 7,619,089 B2 | 11/2009 | Dargazanli et al. | |
| 7,700,585 B2 | 4/2010 | Dargazanli et al. | |
| 2006/0223861 A1 | 10/2006 | Dargazanli et al. | |
| 2006/0223885 A1 | 10/2006 | Dargazanli et al. | |
| 2007/0197601 A1 | 8/2007 | Dargazanli et al. | |
| 2009/0258899 A1 | 10/2009 | Dargazanli et al. | |
| 2010/0022548 A1 | 1/2010 | Dargazanli et al. | |

FOREIGN PATENT DOCUMENTS

| | | |
|---|---|---|
| EP | 0 365 030 | 4/1990 |
| EP | 0 366 006 | 5/1990 |
| EP | 0499995 | 8/1992 |
| EP | 0 556 672 | 8/1993 |
| WO | WO 92/12128 | 7/1992 |
| WO | WO 99/45011 | 10/1999 |
| WO | WO 03/089411 | 10/2003 |
| WO | WO 2006/110724 | 10/2006 |

OTHER PUBLICATIONS

Silverman "Organic chemistry of drug design and drug action" p. 65-73 (1993).*
Hashimoto "Glycine transporter inhibitors . . . " Recent Patents on CNS drug discovery vo.1, p. 43-53 (2006).*
Gilfillan et al. "Glycine transporters . . . " Top Med. chem. v. 4, p. 223-247 (2009).*
Lindsley et al. "Design, synthesis . . . " Chem. Med. Chem. v. 1, p. 807-811 (2006).*
Froelich, O., et, al., Asymmetric Synthesis, 39. 1 Synthesis of 2-(1-Aminoalkyl)Piperidines via 2-Cyano-6-Phenyl Oxazolopiperidine, J. Org. Chem. (1996) vol. 61, pp. 6700-6705.
Jonathan H. Lebowitz, A breach in the blood-brain barrier, PNAS (2005, pp. 14485-14486, vol. 102, No. 41).
Mel R., Optical Isomers , Optical Isomers Newton BBS, (2006), Newton.dep.ant.gov.
Richard Daneman et al., The Blood-Brain Barrier—Lessons from Moody Flies, Cell (2005, pp. 9-12, vol. 123, No. 1).

(Continued)

*Primary Examiner* — Celia Chang
(74) *Attorney, Agent, or Firm* — Kelly L. Bender

(57) ABSTRACT

This invention discloses and claims a compound of general formula (I)

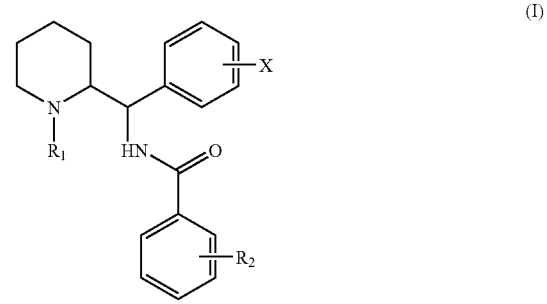

in which $R_1$ represents either a hydrogen atom, or an optionally substituted alkyl group, or a cycloalkylalkyl group, or an optionally substituted phenylalkyl group, or an alkenyl group, X represents a hydrogen atom or one or more substituents chosen from halogen atoms and trifluoromethyl, alkyl and alkoxy groups, $R_2$ represents one or more substituents chosen from halogen atoms, optionally substituted alkoxy and optionally substituted amino. The compounds of this invention exhibit therapeutic utility.

16 Claims, No Drawings

OTHER PUBLICATIONS

Wilson L. Caulfield at al., The First Potent and Selective Inhibitors of the Glycine Transporter Type 2, Journal of Medicinal Chemistry (2001, pp. 2679-2682, vol. 44, No. 17).

Woods, et. al., Method of Treating Schizophrenia Prodome, CA 145:432223 (2006).

Wermuth et al, Molecular variations based on isoteric replacements, The Practice of Medicinal Chemistry; 1996; pp. 203-207.

Balboni et al, Synthesis and activity of 3-pyridylamine ligands at central nicotinic receptors, Eur. J. Med. Chem., 2000 (35) pp. 979-988.

Beak et al, Alpha-Lithioamine Synthetic Equivalents: Syntheses of Diastereoisomers from Boc Derivatives of Cyclic Amines, J. Org. Chem. 1993, 58, pp. 1109-1117.

Beak et al, Alpha-Lithioamine Synthetic Equivalents: Syntheses of Diastereoisomers from the Boc Piperidines, J. Org. Chem. 1990, 55, pp. 2578-2580.

Braga et al, Making crystals from crystals: a green route to crystal engineering and polymorphism, Chem. Commun., 2005 pp. 3635-3645.

Dutta et al, Potent and Selective Ligands for the Dopamine Transporter (DAT): Structure-Activity Relationship Studies of Novel 4-[2-(Diphenylmethoxy)ethyl]-1-(3-phenylpropyl)piperidine Analogues, J. Med. Chem., 1998 (41) pp. 699-705.

Harsing et al, Glycine Transporter Type-1 and its Inhibitors, Current Medicinal Chemistry, 2006 (13) pp. 1017-1044.

Hodgson et al, III. 3-Nitro-4-amino- and the 3:4-Dihalogenobenzaldehydes, J. Chem. Soc. 1927, pp. 20-27.

Javitt et al, Reversal of Phencyclidine-Induced Effects by Glycine and Glycine Transport Inhibitors, Biol. Psychiatry, 1999 (45) pp. 668-679.

Jeong et al, A New Method for the Preparation of Perfluoroalkylated Triphenylethylene Derivatives, Tetrahedron Letters, 1996 (37) 33, pp. 5905-5908.

Leonetti, M., et. al., 2-Chloro-N-[(S)-Phenyl [(2S)-Piperidin-2-YL] Methyl]-3-Trifluoromethyl Benzamide, Monohydrochloride, an inhibitor of the Glycine Transporter Type 1, Increases Evoked-Dopamine Release in the Rat Nucleus Accumbens In Vivo Via an Enhanced Glutamatergic Neurotransmission, Neuroscience, vol. 137, (2006) pp. 555-564.

Martinelli et al, Aromatic Chlorination of p-Aminobenzoic Acid Derivatives, Improved Syntheses of Mono- and Dichloromethotrexate, J. Org. Chem. 1980 (45) pp. 527-529.

Niemers et al, Pyridylalkyl-substiuierte Amine, Synthesis, Sep. 1976, pp. 593-595.

Ohmomo et al, Synthesis and Evaluation of Iodinated Benzamide Derivatives as Selective and Reversible Monoamine Oxidase B Inhibitors, Chem. Pharm. Bull. 1992 (40) 7, pp. 1789-1792.

Sato et al, A new entry to 9-azabicyclo[3.3.1]nonanes using radical translocation/cyclisation reactions of 2-(but-3-ynyl)-1-(o-iodobenzoyl)piperidines, J. Chem. Soc., Perkin Trans 1, 2002, pp. 1438-1443.

Shimada et al, Synthesis and Gastric Antisecretory Activity of N-cyano-N'-(phenyl-pyridinaylmethyl)guanidine Derivatives, Chem. Pharm. Bull., 1984 (32)12 pp. 4893-4906.

Stewart et al, Synthesis of Substituted 9-Oxo-9,10-dihydroacridine-4-carboxylic Acids. I. Factors Affecting the Direction of Ring Closure of Substituted N-(2-Carboxyphenylamino)benzoic Acids, Aust. J. Chem., 1984 (37) pp. 1939-1950.

Sur, et. al.,, Glycine Transporter I Inhibitors and Modulation of NMDA Receptor-Mediated Excitatory Neurotransmission, Current Drug Targets, 2007 (8) pp. 643-649.

Thai et al, Asymmetric Synthesis and Pharmacology of Methylphenidate and Its Para-Substituted Derivatives, J. Med. Chem., 1998 (41) pp. 591-601.

* cited by examiner

N-[PHENYL(PIPERIDIN-2-YL)METHYL] BENZAMIDE DERIVATIVES, PREPARATION THEREOF, AND USE THEREOF IN THERAPY

This application is a continuation of U.S. application Ser. No. 11/045,247, filed Jan. 28, 2005, now allowed, which is a continuation of International application No. PCT/FR2003/002,356, filed Jul. 25, 2003; which claims the benefit of priority of French Patent Application No. 02/09,588, filed Jul. 29, 2002, all of which are incorporated herein by reference in their entirety.

BACKGROUND OF THE INVENTION

Field of the Invention

This invention relates to a series of N-[phenyl(piperidin-2-yl)methyl]benzamide derivatives, their preparation and their application in therapy.

SUMMARY OF THE INVENTION

The compounds of the invention correspond to the general formula (I)

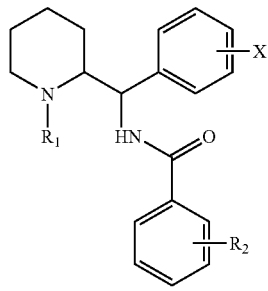

(I)

in which
$R_1$ represents either a hydrogen atom, or a linear or branched $(C_1-C_7)$alkyl group optionally substituted with one or more fluorine atoms, or a $(C_3-C_7)$cycloalkyl-$(C_1-C_3)$alkyl group, or a phenyl$(C_1-C_3)$alkyl group optionally substituted with one or two methoxy groups, or a $(C2-C_4)$alkenyl group, or a $(C_2-C_4)$alkynyl group,
X represents a hydrogen atom or one or more substituents chosen from halogen atoms and trifluoromethyl, linear or branched $(C_1-C_4)$alkyl and $(C_1-C_4)$ alkoxy groups,
$R_2$ represents one or more substituents chosen from halogen atoms, from the groups of general formula $OR_3$ in which $R_3$ represents a hydrogen atom, a $(C_1-C_4)$alkyl group, a phenyl $(C_1-C_3)$alkyl group, or a group of general formula $(CH_2)_n$—$NR_4R_5$ in which n represents the number 2, 3 or 4 and $R_4$ and $R_5$ each represent, independently of each other, a hydrogen atom or a $(C_1-C_4)$alkyl group or form, with the nitrogen atom carrying them, a pyrrolidine, piperidine or morpholine ring, and from the amino groups of general formula $NR_6R_7$ in which $R_6$ and $R_7$ each represent, independently of each other, a hydrogen atom or a $(C_1-C_4)$alkyl group, a phenyl group or a phenyl$(C_1-C_3)$alkyl group, or form, with the nitrogen atom carrying them, a pyrrolidine, piperidine or morpholine ring.

The compounds of general formula (I) may exist in the form of the threo racemate (1R,2R; 1S,2S) or in the form of enantiomers (1R,2R) or (1S,2S); they may exist in the form of free bases or of addition salts with acids.

DETAILED DESCRIPTION OF THE INVENTION

Compounds having a structure which is analogous to that of the compounds of the invention are described in patent U.S. Pat. No. 5,254,569 as analgesics, diuretics, anticonvulsants, anesthetics, sedatives, cerebroprotective agents, by a mechanism of action on the opiate receptors. Other compounds having an analogous structure are described in Patent Application EP 0499995 as 5-$HT_3$ antagonists which are useful in the treatment of psychotic disorders, neurological diseases, gastric syndromes, nausea and vomiting.

The preferred compounds of the invention are devoid of activity on the opiate or 5-HT3 receptors and exhibit a particular activity as specific inhibitors of the glycine transporters glyt1 and/or glyt2.

The compounds preferred as inhibitors of the glyt1 transporter are of the configuration (1S,2S) with $R_2$ representing one or more halogen atoms, while the compounds preferred as inhibitors of the glyt2 transporter are of the configuration (1R,2R) with $R_2$ representing one or more halogen atoms and an amino group of general formula $NR_6R_7$.

The compounds of general formula (I) in which $R_1$ is different from a hydrogen atom, may be prepared by a method illustrated by scheme 1 which follows.

Scheme 1

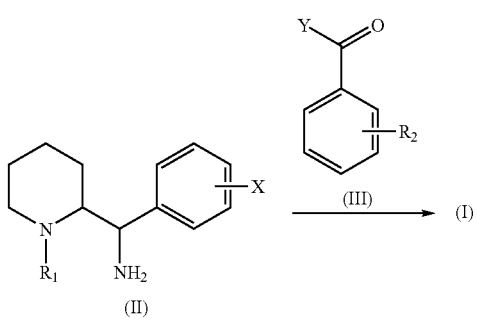

A diamine of general formula (II), in which R, and X are as defined above (with $R_1$ different from a hydrogen atom), is coupled to an activated acid or an acid chloride of general formula (III) in which Y represents an activated OH group or a chlorine atom and $R_2$ is as defined above, using methods known to persons skilled in the art.

The diamine of general formula (II) may be prepared by a method illustrated by scheme 2 which follows.

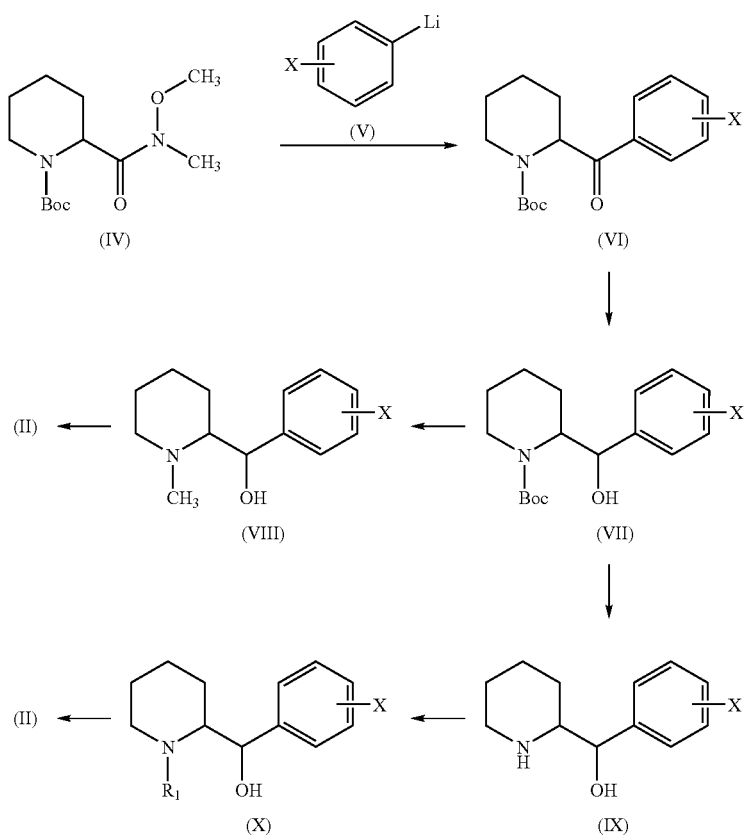

Scheme 2

The Weinreb amide of formula (IV) is reacted with the phenyllithium derivative of general formula (V), in which X is as defined above, in an ethereal solvent such as diethyl ether, between −30° C. and room temperature; a ketone of general formula (VI) is obtained which is reduced to an alcohol with the threo configuration of general formula (VII) with a reducing agent such as K-Selectride® or L-Selectride® (potassium or lithium tri-sec-butylborohydride), in an ethereal solvent such as tetrahydrofuran, between −78° C. and room temperature. The carbamate of general formula (VII) may then be reduced to a threo N-methylaminoalcohol of general formula (VIII) by the action of a mixed hydride such as lithium aluminum hydride, in an ethereal solvent such as tetrahydrofuran, between room temperature and the reflux temperature. The threo alcohol of general formula (VIII) is then converted to a threo intermediate of general formula (II) where $R_1$ represents a methyl group, in two steps: the alcohol functional group is first of all converted to a leaving group, for example a methanesulfonate group, by the action of methylsulfonyl chloride, in a chlorinated solvent such as dichloromethane, and in the presence of a base such as triethylamine, between 0° C. and room temperature, and then the leaving group is reacted with liquefied ammonia at −50° C., in an alcohol such as ethanol, in a closed medium such as an autoclave, between −50° C. and room temperature.

It is also possible to deprotect the carbamate of general formula (VII) by means of a strong base such as aqueous potassium hydroxide, in an alcohol such as methanol in order to obtain the threo amino alcohol of general formula (IX), and to then carry out an N-alkylation by means of a halogenated derivative of formula $R_1Z$, in which $R_1$ is as defined above, but different from a hydrogen atom, and Z represents a halogen atom, in the presence of a base such as potassium carbonate, in a polar solvent such as N,N-dimethylformamide, between room temperature and 100° C. The alcohol of general formula (X) thus obtained is then treated as described for the alcohol of general formula (VIII).

Another variant method, illustrated by scheme 3 which follows, may be used in the case where $R_1$ represents a methyl group and X represents a hydrogen atom. The pyridine oxime of formula (XI) is quaternized, for example, by the action of methyl trifluoromethanesulfonate, in an ethereal solvent such as diethyl ether, at room temperature. The pyridinium salt thus obtained, of formula (XII), is then subjected to hydrogenation under a hydrogen atmosphere, Scheme 3

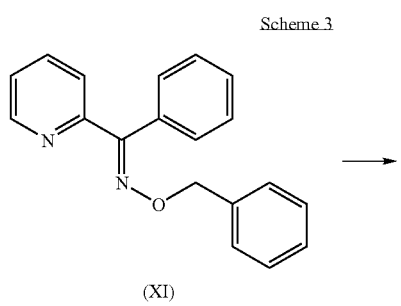

(XI)

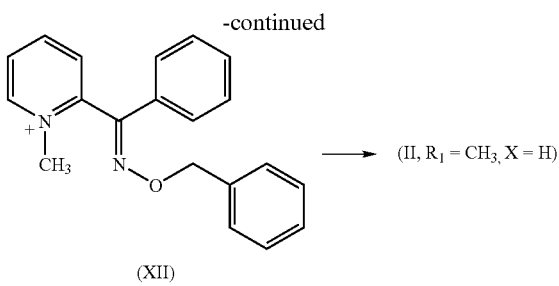

in the presence of a catalyst such as platinum oxide, in a mixture of an alcohol and an aqueous acid such as ethanol and 1 N hydrochloric acid. The diamine of general formula (II) is obtained in which $R_1$ represents a methyl group and X represents a hydrogen atom in the form of a mixture of the two diastereoisomers threo/erythro 9/1. It is possible to salify it, for example, with oxalic acid, and then to purify it by recrystallization of the oxalate formed from a mixture of an alcohol and an ethereal solvent such as methanol and diethyl ether, so as to obtain the pure threo diastereoisomer (1R,2R; 1S,2S).

The compounds of general formula (II) in which $R_1$ represents a hydrogen atom may be prepared by the method illustrated by scheme 4 which follows.

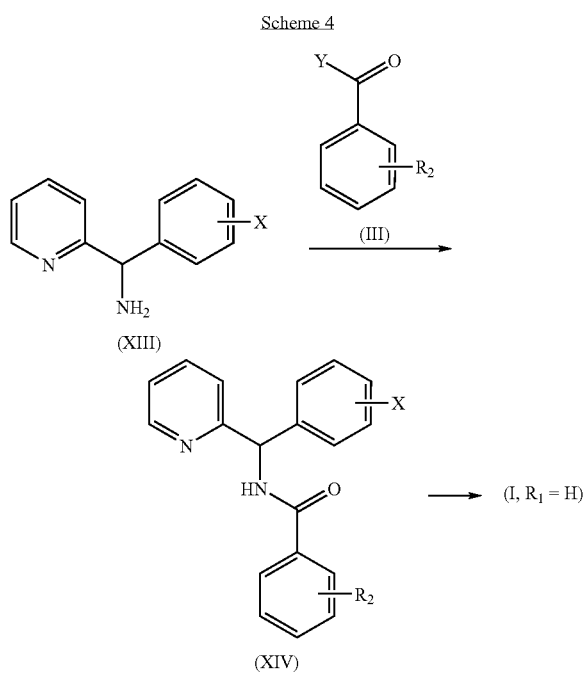

Starting with the amine of general formula (XIII), in which X is as defined above, a coupling is performed with an activated acid or an acid chloride, as described above, of general formula (III) according to methods known to persons skilled in the art, in order to obtain the compound of general formula (XIV). Finally, hydrogenation of the latter is performed, for example with hydrogen in the presence of a catalyst such as 5% platinum on carbon, in an acidic solvent such as glacial acetic acid, so as to obtain a compound of general formula (I) in which R, represents a hydrogen atom.

Another method consists in modifying a compound of general formula (I) in which $R_1$ represents either an optionally substituted phenylmethyl group and in deprotecting the nitrogen of the piperidine ring, for example, with an oxidizing agent or with a Lewis acid, such as boron tribromide, or by hydrogenolysis, or an alkenyl group, preferably allyl, and in deprotecting the nitrogen with a $Pd^0$ complex, in order to obtain a compound of general formula (I) in which $R_1$ represents a hydrogen atom.

Moreover, the chiral compounds of general formula (I) corresponding to the enantiomers (1R,2R) or (1S,2S) of the threo diastereoisomer may also be obtained by separating the racemic compounds by high-performance liquid chromatography (HPLC) on a chiral column, or by resolution of the racemic amine of general formula (II) by the use of a chiral acid, such as tartaric acid, camphorsulfonic acid, dibenzoyltartaric acid or N-acetylleucine, by fractional and preferential recrystallization of a diastereoisomeric salt, from an alcohol type solvent, or alternatively by enantioselective synthesis according to scheme 2 with the use of a chiral Weinreb amide of formula (IV).

The racemic or chiral Weinreb amide of formula (IV), as well as the ketone of general formula (VI), may be prepared according to a method similar to that described in *Eur. J. Med. Chem.*, 35, (2000), 979-988 and *J. Med. Chem.*, 41, (1998), 591-601. The phenyllithium compound of general formula (V) where X represents a hydrogen atom is commercially available. Its substituted derivatives may be prepared according to a method similar to that described in *Tetrahedron Lett.*, 57, 33, (1996), 5905-5908. Also according to a method similar to that described in Patent Application EP-0366006. The amine of general formula (IX) in which X represents a hydrogen atom may be prepared in a chiral series according to a method described in patent U.S. Pat. No. 2,928,835. Finally, the amine of general formula (XIII) may be prepared according to a method similar to that described in *Chem. Pharm. Bull.*, 32, 12, (1984), 4893-4906 and *Synthesis*, (1976), 593-595. All of the references described herein are incorporated herein by reference in their entirety.

Some acids and acid chlorides of general formula (III) are commercially available or, when they are novel, they may be obtained according to methods similar to those described in patents EP-0556672, U.S. Pat. No. 3,801,636, and in *J. Chem. Soc.*, (1927), 25, *Chem. Pharm. Bull.*, (1992), 1789-1792, *Aust. J. Chem.*, (1984), 1938-1950 and *J.O.C.*, (1980), 527. All of these references are incorporated herein by reference in their entirety.

The examples which follow illustrate the preparation of a few compounds of the invention. The elemental microanalyses, the IR and NMR spectra and the HPLC on a chiral column confirm the structures and the enantiomeric purities of the compounds obtained.

The numbers indicated in brackets in the headings of the examples correspond to those of the 1st column of the table given later.

In the names of the compounds, the dash "—" forms part of the word, and the dash "_" only serves for splitting at the end of a line; it is suppressed in the absence of splitting, and should not be replaced either by a normal dash or by a gap.

EXAMPLE 1

Compound No. 65

2,3-Dichloro-N-[(1S)-[(2S)-1-methylpiperidin-2-yl] phenylmethyl]benzamide hydrochloride 1:1

1.1. 1,1-Dimethylethyl (2S)-2-benzoylpiperidine-1-carboxylate

A solution of 1,1-dimethylethyl (2S)-2-(N-methoxy-N-methylcarbamoyl)piperidine-1-carboxylate (11.8 g, 43.3 mmol) in 100 ml of anhydrous diethyl ether is introduced into a 500 ml round-bottomed flask, under a nitrogen atmosphere, the medium is cooled to −23° C., 21.6 ml (43.2 mmol) of a 1.8 M phenyllithium solution in a 70/30 mixture of cyclohexane and diethyl ether are added dropwise and the mixture is stirred at room temperature for 3 h.

After hydrolysis with a saturated aqueous sodium chloride solution, the aqueous phase is separated and it is extracted with ethyl acetate. The organic phase is dried over sodium sulfate, filtered, concentrated under reduced pressure and the residue is purified by chromatography on a silica gel column, eluting with a mixture of ethyl acetate and cyclohexane to obtain 4.55 g of a solid product.

Melting point: 123-125° C.

$[\alpha]_D^{25}=-25.4°$ (c=2.22; $CH_2Cl_2$) ee=97.2%.

1.2. 1,1-Dimethylethyl (1S)-2-[(2S)-hydroxy(phenyl)methyl]piperidine-1-carboxylate A solution of 1,1-dimethylethyl (2S)-2-benzoylpiperidine-1-carboxylate (4.68 g, 16.2 mmol) in 170 ml of anhydrous tetrahydrofuran is introduced into a 500 ml round-bottomed flask, under a nitrogen atmosphere, the solution is cooled to −78° C., 48.5 ml (48.5 mmol) of a 1 M solution of L-Selectride® (lithium tri-sec-butylborohydride) in tetrahydrofuran are added dropwise, and the mixture is stirred at room temperature for 5 h.

It is slowly hydrolyzed in the cold state with 34 ml of water and 34 ml of a 35% aqueous hydrogen peroxide solution, and the mixture is allowed to return to room temperature while it is being stirred for 2 h.

It is diluted with water and ethyl acetate, the aqueous phase is separated, and extracted with ethyl acetate. After washing the combined organic phases, drying over sodium sulfate, filtration and evaporation, the residue is purified by chromatography on a silica gel column, eluting with a mixture of ethyl acetate and cyclohexane to obtain 4.49 g of a pale yellow oil.

$[\alpha]_D^{25}=+63.75°$ (c=0.8; $CH_2Cl_2$) ee=97.8%.

1.3. (1S)-[(2S)-(1-methylpiperidin-2-yl)]phenylmethanol

A solution of lithium aluminum hydride (2.96 g, 78.1 mmol) in 50 ml of anhydrous tetrahydrofuran is introduced into a 200 ml two-necked flask, under a nitrogen atmosphere, the mixture is heated under reflux, 4.49 g (15.4 mmol) of a solution of 1,1-dimethylethyl (1S)-2-[(2S)-hydroxy(phenyl)methyl]piperidine-1-carboxylate in 35 ml of tetrahydrofuran are added and the mixture is kept under reflux for 3.5 h.

It is cooled, it is slowly hydrolyzed with a 0.1 M solution of potassium sodium tartrate and the mixture is kept stirred overnight.

It is filtered and the precipitate is rinsed with tetrahydrofuran, and then the filtrate is concentrated under reduced pressure to obtain 2.95 g of a colorless oily product.

1.4. (1S)-[(2S)-(1-methylpiperidin-2-yl)]phenylmethanamine

A solution of (1S)-[(2S)-(1-methylpiperidin-2-yl)]phenylmethanol (2.95 g, 14.4 mmol) and triethylamine (2 ml, 14.4 mmol) in 70 ml of anhydrous dichloromethane is introduced into a 250 ml round-bottomed flask, under a nitrogen atmosphere, the medium is cooled to 0°0 C., 1.1 ml (14.4 mmol) of methanesulfonyl chloride are added, the mixture is allowed to return slowly to room temperature over 2 h and it is concentrated under reduced pressure.

Liquefied ammonia is introduced into an autoclave provided with magnetic stirring and cooled to −50° C., a solution of crude methanesulfonate prepared beforehand in solution in 30 ml of absolute ethanol is added, the autoclave is closed and the stirring is maintained for 48 h.

The mixture is transferred to a round-bottomed flask, the solvent is evaporated under reduced pressure, and the amine is isolated in the form of an oily product which is used as it is in the next step.

1.5. 2,3-Dichloro-N-[(1S)-[(2S)-1-methylpiperidin-2-yl]phenylmethyl]benzamide hydrochloride 1:1

A solution of 2,3-dichlorobenzoic acid (0.5 g, 2.6 mmol), 1-([3-(dimethylamino)propyl]-3-ethylcarbodiimide hydrochloride (0.5 g, 2.6 mmol) and 1-hydroxybenzotriazole (0.35 g, 2.6 mmol) in 10 ml of dichloromethane is introduced into a 50 ml round-bottomed flask and the mixture is stirred at room temperature for 30 min.

A solution of (1S)-[(2S)-(1-methylpiperidin-2-yl)]phenylmethanamine (0.53 g, 2.5 mmol) in a few ml of dichloromethane is added to the above mixture and the stirring continued for 5 h.

The mixture is treated with water and extracted several times with dichloromethane. After washing the organic phases with water and then with a 1N aqueous sodium hydroxide solution, drying over magnesium sulfate, filtration and evaporation of the solvent under reduced pressure, the residue is purified by chromatography on a silica gel column, eluting with a mixture of dichloromethane and methanol. 0.52 g of oily product is obtained which is isolated in hydrochloride form from a 0.1N hydrochloric acid solution in propan-2-ol.

0.5 g of hydrochloride is finally isolated in the form of a white solid.

Melting point: 124-126° C.

$[\alpha]_D^{25}=+66.30$ (c=0.58; $CH_3OH$).

EXAMPLE 2

Compound No. 55

4-Amino-3,5-dichloro-N-[(1R)-[(2R)-1-methylpiperidin-2-yl]phenylmethyl]benzamide hydrochloride 1:1

2.1. 2-(Benzyloxyiminophenylmethyl)-1-methylpyridinium trifluoromethanesulfonate 17.4 ml (120 mmol) of methyl trifluoromethanesulfonate are added dropwise at 0° C. to a suspension of 35 g (120 mmol) of phenyl(pyridin-2-yl)methanone O-benzyloxime in 200 ml of diethyl ether, and the mixture is stirred at room temperature for 3 h.

The precipitate formed is recovered by filtration and it is dried under reduced pressure to obtain 49 g of product, which product is used as it is in the next step.

2.2. threo-(1-Methylpiperidin-2-yl)phenylmethanamine ethanedioate 2:1

A solution of 2-(benzyloxyiminophenylmethyl)-1-methylpyridinium trifluoromethanesulfonate (14.8 g, 31.89 mmol) and 0.74 g of platinum oxide in 50 ml of ethanol and 50 ml of 1 N hydrochloric acid is placed in a Parr flask, and hydrogenation is performed for 5 h.

The ethanol is evaporated under reduced pressure, the residue is extracted with dichloromethane, the aqueous phase is separated, a solution of ammonia is added thereto and it is extracted with dichloromethane. After washing the combined organic phases, drying over sodium sulfate, filtration and evaporation of the solvent under reduced pressure, 6.7 g of an oily product comprising 10% of erythro diastereoisomer are obtained.

The ethanedioate is prepared by dissolving the above isolated 6.7 g of base in methanol, and by the action of two equivalents of ethanedioic acid dissolved in the minimum amount of methanol.

The salt obtained is purified by recrystallization from a mixture of methanol and diethyl ether to isolate 4.7 g of pure ethanedioate of the threo diastereoisomer.

Melting point: 156-159° C.

2.3. (1R)-[(2R)-(1-methylpiperidin-2-yl)]phenyl-methanamine

A solution of threo-(1-methylpiperidin-2-yl)phenylmethanamine (80 g, 390 mmol) in 300 ml of methanol, and a solution of N-acetyl-D-leucine (68 g, 390 mmol) in 450 ml of methanol are introduced into a 4 l round-bottom flask. The solution is concentrated under reduced pressure and the residue is recrystallized from 1100 ml of propan-2-ol to obtain 72 g of salts of (1R)-[(2R)-(1-methylpiperidin-2-yl)]phenylmethanamine.

The recrystallization is repeated three more times to obtain 15 g of additional salt of (1R)-[(2R)-(1-methylpiperidin-2-yl)]phenylmethanamine.

Melting point: 171.5° C.

$[\alpha]_D^{25} = -11°$ (c=1; $CH_3OH$) ee>99%.

2.4. 4-Amino-3,5-dichloro-N-[(1R)-[(2R)-1-methylpiperidin-2-yl]phenylmethyl]-3,5-dichlorobenzamide hydrochloride 1:1

Employing the procedure described in step 1.6 of Example 1 above, and starting with 2.18 g (11.65 mmol) of 4-amino-3,5-dichlorobenzoic acid, 2.23 g (10.6 mmol) of 1-[3-(dimethylamino)propyl]-3- ethylcarbodiimide hydrochloride, 1.41 g (10.6 mmol) of 1-hydroxybenzotriazole and 2.16 g (10.6 mmol) of (1R)-[(2R)-methylpiperidin-2-yl]phenylmethanamine, 3.92 g of the title compound are obtained in base form.

The hydrochloride thereof is prepared using a 0.1 N hydrochloric acid solution in propan-2-ol to obtain 3.94 g of the hydrochloride in the form of a white solid.

Melting point: 250-260° C.

$[\alpha]_D^{25} = +24.5°$ (c=0.9; $CH_3OH$).

EXAMPLE 3

Compound No. 59

3,5-Dichloro-N-[(1-methylpiperidin-2-yl)phenylmethyl]-4-(pyrrolidin-1-yl)benzamide hydrochloride 1:1

3.1. 3,5-Dichloro-4-fluorobenzoic acid.

A solution of 3,5-dichloro-4-fluoro[(trifluoromethyl)benzene] (5 g, 21.46 mmol) in 10 ml of concentrated sulfuric acid is introduced into an autoclave and the solution is heated at 120° C. overnight.

After cooling, the mixture is taken up in water, the precipitate formed is recovered by filtration and it is dried under reduced pressure.

The title acid is quantitatively obtained, which acid is used as it is in the next step.

3.2. 3,5-Dichloro-4-(pyrrolidin-1-yl)benzoic acid 1 g (4.8 mmol) of 3,5-dichloro-4-fluorobenzoic acid, 1.56 g (4.8 mmol) of cesium carbonate and 1 ml (12 mmol) of pyrrolidine in solution in 5 ml of dimethyl sulfoxide are introduced into a 100 ml round-bottom flask and the mixture is heated at 125° C. overnight.

After cooling, it is hydrolyzed with concentrated hydrochloric acid, the precipitate formed is recovered by filtration and it is dried under reduced pressure to obtain 0.65 g of title acid.

3.3. 3,5-Dichloro-N-[(1-methylpiperidin-2-yl)phenylmethyl]-4-(pyrrolidin-1-yl)benzamide hydrochloride 1:1

Using the procedure described in step 1.6 of Example 1 above, and starting with 0.5 g (2 mmol) of 3,5-dichloro-4-(pyrrolidin-1-yl)benzoic acid, 0.35 g (1.82 mmol) of 1-[3-(dimethylamino)propyl]-3-ethylcarbodiimide hydrochloride, 0.25 g (1.82 mmol) of 1-hydroxybenzotriazole and 0.37 g (1.82 mmol) of threo-(1-methylpiperidin-2-yl)]phenylmethanamine, 0.1 g of product is obtained in base form.

The hydrochloride thereof is prepared from a 0.1 N hydrochloric acid solution in propan-2-ol.

0.85 g of hydrochloride is finally isolated in the form of a white solid.

Melting point: 157-159° C.

EXAMPLE 4

Compound No. 76

2,3-Dichloro-N-[(S)-phenyl[(2S)-piperidin-2-yl]methyl]benzamide

4.1. (S)-Phenyl[(2S)-piperidin-2-yl]methanol

A solution of 2.0 g (6.9 mmol) of 1,1-dimethylethyl (1S)-2-[(2S)-hydroxy(phenyl)methyl)-piperidine-1-carboxylate (obtained according to the procedure described in step 1.2 of Example 1) in 40 ml of methanol is placed in a 250 ml round-bottom flask, an aqueous potassium hydroxide solution prepared from 2 g of potassium hydroxide pellets and 20 ml of water is added, and the mixture is heated under reflux for 2 h.

It is cooled, the solvent is evaporated off under reduced pressure, water is added and the mixture is extracted several times with dichloromethane. After washing the combined organic phases, drying on magnesium sulfate, filtration and evaporation of the solvent under reduced pressure, 1 g of a white solid is obtained.

Melting point: 148-150° C.

$[\alpha]_D^{25} = +38.40$ (c=0.98; $CHCl_3$).

4.2. (S)-[(2S)-1-Allylpiperidin-2-yl](phenyl)methanol 2.6 g (13.58 mmol) of (S)-phenyl[(2S)-piperidin-2-yl]methanol and 100 ml of acetonitrile are introduced into a 500 ml round-bottom flask provided with magnetic stirring and purged with argon. 2.8 g of potassium carbonate and 1.4 ml (1.2 eq.) of allyl bromide are then added to the suspension obtained, and the stirring is maintained at 25° C. for 6 h.

100 ml of water and 100 ml of ethyl acetate are added, the aqueous phase is separated, it is extracted three times with 50 ml of ethyl acetate, the combined organic phases are washed with 100 ml of water and then 100 ml of a saturated aqueous sodium chloride solution, dried over sodium sulfate, filtered and the solvent is evaporated off under reduced pressure.

3 g of a yellow oil are obtained, which oil is purified by chromatography on a silica gel column (120 g, elution gradient from 2% to 10% of methanol in dichloromethane over 30 min).

2.7 g of product are isolated in the form of a yellow oil.

4.3. (S)-[(2S)-1-Allylpiperidin-2-yl](phenyl)-methanamine 2.7 g (11.67 mmol) of (S)-[(2S)-1-allylpiperidin-2-yl](phenyl)methanol and 1.62 ml of triethylamine in 80 ml of anhydrous dichloromethane are introduced into a 250 ml round-bottom flask, under a nitrogen atmosphere, the medium is cooled to 0° C., 0.9 ml of methylsulfonyl chloride is added, the mixture is allowed to return slowly to room temperature over 2 h and it is concentrated under reduced pressure.

Liquefied ammonia is introduced into an autoclave provided with magnetic stirring and cooled to −50° C., a solution of crude methanesulfonate previously prepared in solution in 30 ml of absolute ethanol is added, the autoclave is closed and the stirring is maintained for 48 h.

The mixture is poured into a round-bottom flask, it is concentrated under reduced pressure and 1.5 g of amine are isolated in the form of an oily product which is used as it is in the next step.

4.4. N-[(S)-[(2S)-1-Allylpiperidin-2-yl](phenyl)-methyl]-2,3-dichlorobenzamide 5 ml of dichloromethane, 0.13 g (0.68 mmol) of 2,3-dichlorobenzoic acid, 0.13 g (0.68 mmol) of 1-[3-(dimethylamino)propyl]-3-ethylcarbodiimide hydrochloride and 0.085 g of dimethylaminopyridine are successively introduced into a 10 ml round-bottom flask, and the mixture is stirred at room temperature for 30 min.

0.18 g of (S)-[(2S)-1-allylpiperidin-2-yl](phenyl)methanamine in solution in a few ml of dichloromethane is added and the stirring is continued for 24 h. 5 ml of water are added, the mixture is filtered on a Whatman® cartridge (PTFE) and purified directly on a cartridge of 10 g of silica, eluting with a 98/2 to 90/10 mixture of dichloromethane and methanol.

0.18 g of base is isolated in the form of a colorless oil.

4.5. 2,3-Dichloro-N-[(S)-phenyl[(2S)-piperidin-2-yl]methyl]benzamide 0.21 g (3 eq.) of 1,3-dimethylbarbituric acid in solution in 3 ml of anhydrous dichloromethane is introduced into a 10 ml round-bottom flask provided with mechanical stirring, under an argon atmosphere, 0.005 g (0.01 eq.) of tetrakis(triphenylphosphine)-palladium (0) is added and the mixture is heated at 30° C.

A solution of 0.18 g (0.3 mmol) of N-[(S)-[(2S)-1-allylpiperidin-2-yl](phenyl)methyl]-2,3-dichlorobenzamide in 1 ml of dichloromethane is added and the mixture is kept stirring for 24 h.

3 ml of a saturated aqueous sodium hydrogen sulfate solution are added, the mixture is filtered on a Whatman® cartridge (PTFE) and purified directly on a cartridge of 10 g of silica, eluting with dichloromethane containing 0.4% of a 33% ammonia solution.

0.1 g of base is isolated, which base is salified with a 0.1 N hydrochloric acid solution in propan-2-ol.

0.076 g of hydrochloride is obtained which is purified in a reversed phase on an XTerra® MS C18 column (pH 10).

0.037 g of base is finally isolated in the form of white crystals.

Melting point: 156-158° C.

The table that follows lists the chemical structures and the physical properties of a few compounds of the invention.

In the "$R_2$" column of this table, "piperid" denotes a piperidin-1-yl group, "pyrrolid" denotes a pyrrolidin-1-yl group and "morphol" denotes a morpholin-4-yl group.

In the "Salt" column, "−" denotes a compound in base state and "HCl" denotes a hydrochloride; the acid:base molar ratio is indicated opposite.

The optical rotations of the optically pure compounds are as follows

| No. | Stereochemistry | $[\alpha]_D^{20}$ | (°, $CH_3OH$) |
|-----|-----------------|-------------------|----------------|
| 41  | threo (1S, 2S)  | −73.3             | c = 0.225      |
| 55  | threo (1R, 2R)  | +24.5             | c = 0.9        |
| 64  | threo (1S, 2S)  | +13.2             | c = 0.84       |
| 65  | threo (1S, 2S)  | +66.3             | c = 0.58       |
| 71  | threo (1S, 2S)  | +73.9             | c = 0.89       |
| 72  | threo (1R, 2R)  | −97.0             | c = 1          |
| 74  | threo (1R, 2R)  | −104.4            | c = 1          |

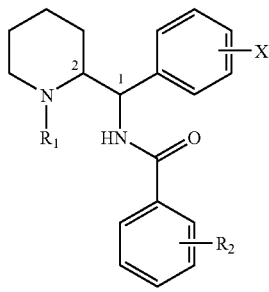

| No. | Stereochemistry | $R_1$ | X | $R_2$ | Salt | M.p. (° C.) |
|-----|-----------------|-------|---|-------|------|-------------|
| 1   | threo (1R, 2R; 1S, 2S) | $CH_3$ | H | 3-$OCH_3$, 4-Cl | — | 159-161 |
| 2   | threo (1R, 2R; 1S, 2S) | $CH_3$ | H | 3-I, 4-Cl | — | 102-104 |

-continued

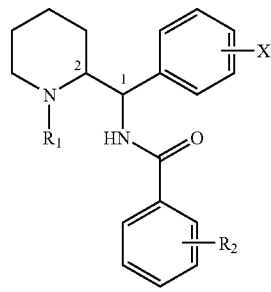

| No. | Stereochemistry | R₁ | X | R₂ | Salt | | M.p. (° C.) |
|---|---|---|---|---|---|---|---|
| 3 | threo (1R, 2R; 1S, 2S) | CH₃ | H | 4-Cl | — | | 149.5-150.5 |
| 4 | threo (1R, 2R; 1S, 2S) | CH₃ | H | 3,5-Cl₂ | HCl | 1:1 | 152-154 |
| 5 | threo (1R, 2R; 1S, 2S) | CH₃ | H | 4-N(CH₃)₂ | — | | 128-130 |
| 6 | threo (1R, 2R; 1S, 2S) | CH₃ | H | 3,4-Cl₂ | — | | 50-52 |
| 7 | threo (1R, 2R; 1S, 2S) | CH₃ | H | 3,4-(OCH₃)₂ | HCl | 1:1 | 68-70 |
| 8 | threo (1R, 2R; 1S, 2S) | CH₃ | H | 3,4-F₂ | HCl | 1:1 | 62-64 |
| 9 | threo (1R, 2R; 1S, 2S) | CH₃ | H | 3-F | HCl | 1:1 | 36-38 |
| 10 | threo (1R, 2R; 1S, 2S) | CH₃ | H | 3-Br | HCl | 1:1 | 116-118 |
| 11 | threo (1R, 2R; 1S, 2S) | CH₃ | H | 3,5-Cl₂, 4-OH | — | | 266-268 |
| 12 | threo (1R, 2R; 1S, 2S) | CH₃ | H | 3-N(CH₃)₂ | HCl | 1:1 | 87-88 |
| 13 | threo (1R, 2R; 1S, 2S) | CH₃ | H | 3,5-Cl₂, 4-NH₂ | — | | 170-171 |
| 14 | threo (1R, 2R; 1S, 2S) | CH₃ | H | 3-Br, 4-OCH₃ | HCl | 1:1 | 136-137 |
| 15 | threo (1R, 2R; 1S, 2S) | CH₃ | H | 2,4,6-Cl₃ | — | | 97-104 |
| 16 | threo (1R, 2R; 1S, 2S) | CH₃ | H | 2,3-Cl₂ | — | | 107-114 |
| 17 | threo (1R, 2R; 1S, 2S) | CH₃ | H | 2-Cl | — | | 126-130 |
| 18 | threo (1R, 2R; 1S, 2S) | CH₃ | H | 2,4-Cl₂ | — | | 138-142 |
| 19 | threo (1R, 2R; 1S, 2S) | CH₃ | H | 2-Cl, 4-Br | — | | 143-145 |
| 20 | threo (1R, 2R; 1S, 2S) | CH₃ | H | 2,5-Cl₂ | — | | 133-134 |
| 21 | threo (1R, 2R; 1S, 2S) | CH₃ | H | 2,6-Cl₂ | — | | 138-143 |
| 22 | threo (1R, 2R; 1S, 2S) | CH₃ | H | 2,3,5-Cl₃ | — | | 156-159 |
| 23 | threo (1R, 2R; 1S, 2S) | CH₃ | H | 2-NH₂, 3,5-Cl₂ | HCl | 1:1 | 186-188 |
| 24 | threo (1R, 2R; 1S, 2S) | CH₃ | H | 2-Cl, 5-NH₂ | HCl | 1:1 | 266-268 |
| 25 | threo (1R, 2R; 1S, 2S) | CH₃ | H | 3-Cl, 4-NH₂ | HCl | 1:1 | 164-166 |
| 26 | threo (1R, 2R; 1S, 2S) | CH₃ | H | 3-NH₂, 4-Cl | HCl | 1:1 | 230-232 |
| 27 | threo (1R, 2R; 1S, 2S) | CH₃ | H | 2-Cl, 4-NH₂ | HCl | 1:1 | 254-256 |
| 28 | threo (1R, 2R; 1S, 2S) | CH₃ | H | 2-NH₂, 4-Cl | HCl | 1:1 | 236-238 |
| 29 | threo (1R, 2R; 1S, 2S) | CH₃ | H | 2-Cl, 3-NH₂ | HCl | 1:1 | 195-200 |
| 30 | threo (1R, 2R; 1S, 2S) | CH₃ | H | 6-NH₂, 2,5-Cl₂ | HCl | 1:1 | 267-268 |
| 31 | threo (1R, 2R; 1S, 2S) | CH₃ | H | 3,5-Cl₂, 4-O(CH₂)₂piperid | HCl | 2:1 | 44-46 |
| 32 | threo (1R, 2R; 1S, 2S) | CH₃ | H | 3,5-Cl₂, 4-O(CH₂)₃N(CH₃)₂ | HCl | 2:1 | 39-41 |
| 33 | threo (1R, 2R; 1S, 2S) | CH₃ | H | 3,5-Cl₂, 4-O(CH₂)₂N(CH₃)₂ | HCl | 2:1 | 130-132 |
| 34 | threo (1R, 2R; 1S, 2S) | CH₃ | H | 3,5-Cl₂, 4-O(CH₂)₂pyrrolid | HCl | 2:1 | 78-80 |
| 35 | threo (1R, 2R; 1S, 2S) | CH₃ | H | 3,5-Cl₂, 4-O(CH₂)₂morphol | HCl | 2:1 | 166-168 |
| 36 | threo (1R, 2R; 1S, 2S) | CH₃ | H | 2-Cl, 6-F | HCl | 1:1 | 266-268 |
| 37 | threo (1R, 2R; 1S, 2S) | CH₃ | H | 3,5-Cl₂, 4-N(CH₃)₂ | HCl | 1:1 | 157-159 |
| 38 | threo (1R, 2R; 1S, 2S) | CH₃ | H | 2-Cl, 5-I | HCl | 1:1 | 281-285 |
| 39 | threo (1R, 2R; 1S, 2S) | CH₃ | H | 3,5-Cl₂, 4-NHCH₂CH₃ | HCl | 1:1 | 175-180 |
| 40 | threo (1R, 2R; 1S, 2S) | CH₃ | H | 3-Cl, 4-I | HCl | 1:1 | 98-99 |
| 41 | threo (1S, 2S) | CH₃ | H | 3,5-Cl₂, 4-NH₂ | — | | 176-177 |
| 42 | threo (1R, 2R; 1S, 2S) | CH₃ | H | 2-I, 4-Cl | — | | 213-214 |
| 43 | threo (1R, 2R; 1S, 2S) | CH₃ | H | 3-Cl, 4-OH | HCl | 1:1 | 194-195 |
| 44 | threo (1R, 2R; 1S, 2S) | CH₃ | H | 3-Cl, 4-piperid | HCl | 1:1 | 270-272 |
| 45 | threo (1R, 2R; 1S, 2S) | CH₃ | H | 2-OCH₃, 3,5-Cl₂ | — | | 97-98 |
| 46 | threo (1R, 2R; 1S, 2S) | CH₃ | H | 2-Cl, 3,4-(OCH₃)₂ | — | | 229-230 |
| 47 | threo (1R, 2R; 1S, 2S) | CH₃ | H | 2-Br, 4-F | — | | 124-125 |
| 48 | threo (1R, 2R; 1S, 2S) | CH₃ | H | 3-Cl, 4-pyrrolid | HCl | 1:1 | 154-156 |
| 49 | threo (1R, 2R; 1S, 2S) | CH₃ | H | 2-Br, 5-Cl | — | | 156-157 |
| 50 | threo (1R, 2R; 1S, 2S) | CH₃ | H | 2-Br | — | | 202-203 |
| 51 | threo (1R, 2R; 1S, 2S) | CH₃ | H | 2-Br, 4,5-(OCH₃)₂ | — | | 218-219 |
| 52 | threo (1R, 2R; 1S, 2S) | CH₃ | H | 2-Cl, 3,6-F₂ | — | | 52-53 |
| 53 | threo (1R, 2R; 1S, 2S) | CH₃ | H | 3-Cl, 4-morphol | HCl | 1:1 | 158-162 |
| 54 | threo (1R, 2R; 1S, 2S) | CH₃ | H | 3,5-Cl, 4-piperid | HCl | 1:1 | 154-163 |
| 55 | threo (1R, 2R) | CH₃ | H | 3,5-Cl₂, 4-NH₂ | HCl | 1:1 | 250-260 |
| 56 | threo (1R, 2R; 1S, 2S) | CH₃ | H | 2-I, 3-Cl | HCl | 1:1 | 253-255 |
| 57 | threo (1R, 2R; 1S, 2S) | CH₃ | H | 2-Cl, 3-I | HCl | 1:1 | 297-298 |
| 58 | threo (1R, 2R; 1S, 2S) | CH₃ | H | 3,5-Cl₂, 4-NHC₆H₅ | HCl | 1:1 | 236-240 |
| 59 | threo (1R, 2R; 1S, 2S) | CH₃ | H | 3,5-Cl₂, 4-pyrrolid | HCl | 1:1 | 157-159 |
| 60 | threo (1R, 2R; 1S, 2S) | CH₃ | H | 2-Cl, 6-F | HCl | 1:1 | 271-272 |
| 61 | threo (1R, 2R; 1S, 2S) | CH₃ | H | 2-Cl, 4,5-(OCH₃)₂ | — | | 242-243 |
| 62 | threo (1R, 2R; 1S, 2S) | CH₃ | H | 2-Cl, 4-F | HCl | 1:1 | 365-366 |
| 63 | threo (1R, 2R; 1S, 2S) | CH₃ | H | 2-Br, 5-OCH₃ | — | | 213-214 |
| 64 | threo (1S, 2S) | CH₃ | H | 3,5-Cl₂, 4-N(CH₃)₂ | HCl | 1:1 | 158-168 |

-continued

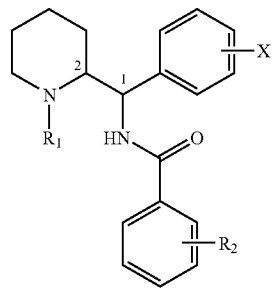

| No. | Stereochemistry | R₁ | X | R₂ | Salt | | M.p. (° C.) |
|---|---|---|---|---|---|---|---|
| 65 | threo (1S, 2S) | CH₃ | H | 2,3-Cl₂ | HCl | 1:1 | 124-126 |
| 66 | threo (1R, 2R; 1S, 2S) | CH₃ | H | 3,5-(OCH₃)₂, 4-OCH₂C₆H₅ | HCl | 1:1 | 274-275 |
| 67 | threo (1R, 2R; 1S, 2S) | CH₃ | H | 3,5-Cl₂, 4-OCH₂C₆H₅ | HCl | 1:1 | 165-175 |
| 68 | threo (1R, 2R; 1S, 2S) | CH₃ | H | 3,5-Cl₂, 4-NHCH₂C₆H₅ | HCl | 1:1 | 165-175 |
| 69 | threo (1R, 2R; 1S, 2S) | CH₃ | H | 2-Cl, 3-F | HCl | 1:1 | 115-116 |
| 70 | threo (1R, 2R; 1S, 2S) | CH₃ | H | 2-Cl, 5-F | HCl | 1:1 | 212-215 |
| 71 | threo (1S, 2S) | CH₃ | H | 2-Cl, 4-F | HCl | 1:1 | 123-125 |
| 72 | threo (1R, 2R) | CH₃ | H | 2,5-Cl₂, 6-NH₂ | HCl | 1:1 | 66-67 |
| 73 | threo (1R, 2R; 1S, 2S) | CH₃ | H | 2-Cl, 5-OCH₃, 6-NH₂ | HCl | 1:1 | 258-259 |
| 74 | threo (1R, 2R) | CH₃ | H | 2-Cl, 5-OCH₃, 6-NH₂ | HCl | 1:1 | 138-139 |
| 75 | threo (1R, 2R; 1S, 2S) | CH₃ | H | 2,3-Cl₂, 6-NH₂ | HCl | 1:1 | 230-236 |
| 76 | threo (1S, 2S) | CH₃ | H | 2,3-Cl₂ | — | — | 156-158 |

The compounds of the invention were subjected to a series of pharmacological trials which demonstrated their utility as substances having therapeutic activity.

Study of the Transport of Glycine in SK-N-MC Cells Expressing the Native Human Transporter Glyt1.

The capture of [$^{14}$C]glycine is studied in SK-N-MC cells (human neuroepithelial cells) expressing the native human transporter glyt1 by measuring the radioactivity incorporated in the presence or in the absence of the test compound. The cells are cultured in a monolayer for 48 h in plates pretreated with fibronectin at 0.02%. On the day of the experiment, the culture medium is removed and the cells are washed with a Krebs-HEPES ([4-(2-hydroxyethyl)piperiazine-1-ethanesulphonic acid) buffer at pH 7.4. After a preincubation of 10 min at 37° C. in the presence either of buffer (control batch), or of test compound at various concentrations, or of 10 mM glycine (determination of the nonspecific capture), 10 µM [$^{14}$C]glycine (specific activity 112 mCi/mmol) are then added. The incubation is continued for 10 min at 37° C., and the reaction is stopped by 2 washes with a Krebs-HEPES buffer at pH 7.4. The radioactivity incorporated by the cells is then estimated after adding 100 µl of liquid scintillant and stirring for 1 h. The counting is performed on a Microbeta Tri-lux™ counter. The efficacy of the compound is determined by the IC$_{50}$, the concentration of the compound which reduces by 50% the specific capture of glycine, defined by the difference in radioactivity incorporated by the control batch and the batch which received the glycine at 10 mM.

The compounds of the invention, in this test, have an IC$_{50}$ of the order of 0.001 to 10 µM.

Study ex vivo of the Inhibitory Activity of a Compound on the Capture of [$^{14}$C]glycine in Mouse Cortical Homogenate Increasing doses of the compound to be studied are administered by the oral route (preparation by trituration of the test molecule in a mortar in a solution of Tween/Methocel™ at 0.5% in distilled water) or by the intraperitoneal route (dissolution of the test molecule in physiological saline or preparation by trituration in a mortar in a solution of Tween/Methocel™ at 0.5% in water, according to the solubility of the molecule) to 20 to 25 g Iffa Crédo OF1 male mice on the day of the experiment. The control group is treated with the vehicle. The doses in mg/kg, the route of administration and the treatment time are determined according to the molecule to be studied.

After the animals have been humanely killed by decapitation at a given time after the administration, the cortex of each animal is rapidly removed on ice, weighed and stored at 4° C. or frozen at −80° C. (in both cases, the samples are stored for a maximum of 1 day). Each sample is homogenized in a Krebs-HEPES buffer at pH 7.4 at a rate of 10 ml/g of tissue. 20 µl of each homogenate are incubated for 10 min at room temperature in the presence of 10 mM L-alanine and buffer. The nonspecific capture is determined by adding 10 mM glycine to the control group. The reaction is stopped by filtration under vacuum and the retained radioactivity is estimated by solid scintillation by counting on a Microbeta Tri-lux™ counter.

An inhibitor of the capture of [$^{14}$C]glycine will reduce the quantity of radioligand incorporated into each homogenate. The activity of the compound is evaluated by its ED$_{50}$, the dose which inhibits by 50% the capture of [$^{14}$C]glycine compared with the control group.

The most potent compounds of the invention, in this test, have an ED$_{50}$ of 0.1 to 5 mg/kg by the intraperitoneal route or by the oral route.

Study of the Transport of Glycine in Mouse Spinal Cord Homogenate

The capture of [$^{14}$C]glycine by the transporter glyt2 is studied in mouse spinal cord homogenate by measuring the radioactivity incorporated in the presence or in the absence of the compound to be studied.

After the animals have been humanely killed (Iffa Crédo OF1 male mice weighing 20 to 25 g on the day of the experiment), the spinal cord of each animal is rapidly removed, weighed and stored on ice. The samples are homogenized in a Krebs-HEPES ([4-(2-hydroxyethyl)piperazine-1-ethanesulphonic acid) buffer, pH 7.4, at a rate of 25 ml/g of tissue.

50 µl of homogenate are preincubated for 10 min at 25° C. in the presence of Krebs-HEPES buffer, pH 7.4 and of compound to be studied at various concentrations, or of 10 mM glycine in order to determine the nonspecific capture. The [$^{14}$C]glycine (specific activity=112 mCi/mmol) is then added for 10 min at 25° C. at the final concentration of 10 µM. The reaction is stopped by filtration under vacuum and the radioactivity is estimated by solid scintillation by counting on a Microbeta Tri-lux™ counter. The efficacy of the compound is determined by the concentration $IC_{50}$ capable of reducing by 50% the specific capture of glycine, defined by the difference in radioactivity incorporated by the control batch and the batch which received the 10 mM glycine.

The compounds of the invention in this test have an $IC_{50}$ of the order of 0.001 to 10 µM.

Study ex vivo of the Inhibitory Activity of a Compound on the Capture of [$^{14}$C]glycine in Mouse Spinal Homogenate Increasing doses of the compound to be studied are administered by the oral route (preparation by trituration of the test compound in a mortar, in a solution of Tween/Methocel™ at 0.5% in distilled water) or intraperitoneal route (test compound dissolved in physiological saline, or triturated in a mortar, in a solution of Tween/Methocel™ at 0.5% in distilled water) to 20 to 25 g Iffa Crédo OF1 male mice on the day of the experiment. The control group is treated with the vehicle. The doses in mg/kg, the route of administration, the treatment time and the humane killing time are determined according to the compound to be studied.

After humanely killing the animals by decapitation at a given time after the administration, the spinal cords are rapidly removed, weighed and introduced into glass scintillation bottles, stored on crushed ice or frozen at −80° C. (in both cases, the samples are stored for a maximum of 1 day). Each sample is homogenized in a Krebs-HEPES buffer at pH 7.4, at a rate of 25 ml/g of tissue. 50 µl of each homogenate are incubated for 10 min at room temperature in the presence of buffer.

The nonspecific capture is determined by adding 10 mM glycine to the control group.

The reaction is stopped by filtration under vacuum and the radioactivity is estimated by solid scintillation by counting on a Microbeta Tri-lux™ counter.

An inhibitor of the capture of [$^{14}$C]glycine will reduce the quantity of radioligand incorporated in each homogenate. The activity of the compound is evaluated by its $ED_{50}$, the effective dose which inhibits by 50% the capture of [$^{14}$C]glycine compared with the control group.

The best compounds of the invention have, in this test, an $ED_{50}$ of 1 to 20 mg/kg, by the intraperitoneal route or by the oral route.

The results of the trials carried out on the compounds of the invention having the configuration (1S,2S) and their threo racemates having the configuration (1R,2R; 1S,2S) in the general formula (I) of which $R_2$ represents one or more halogen atoms show that they are inhibitors of the glycine transporter glyt1 which are present in the brain, this being in vitro and ex vivo.

These results suggest that the compounds of the invention can be used for the treatment of behavioral disorders associated with dementia, psychoses, in particular schizophrenia (deficient form and productive form) and acute or chronic extrapyramidal symptoms induced by neuroleptics, for the treatment of various forms of anxiety, panic attacks, phobias, obsessive-compulsive disorders, for the treatment of various forms of depression, including psychotic depression, for the treatment of disorders due to alcohol abuse or to withdrawal from alcohol, sexual behavior disorders, food intake disorders, and for the treatment of migraine.

The results of the trials carried out on the compounds of the invention having the configuration (1R,2R) and their racemates having the configuration (1R,2R; 1S,2S) in the general formula (I) of which $R_2$ represents both a halogen atom and an amino group $NR_6R_7$ show that they are inhibitors of the glycine transporter glyt2, predominantly present in the spinal cord, this being in vitro and ex vivo.

These results suggest that the compounds of the invention may be used for the treatment of painful muscular contractures in rheumatology and in acute spinal pathology, for the treatment of spastic contractures of medullary or cerebral origin, for the symptomatic treatment of acute and subacute pain of mild to moderate intensity, for the treatment of intense and/or chronic pain, of neurogenic pain and rebellious algia, for the treatment of Parkinson's disease and of Parkinsonian symptoms of neurodegenerative origin or induced by neuroleptics, for the treatment of primary and secondary generalized epilepsy, partial epilepsy with a simple or complex symptomatology, mixed forms and other epileptic syndromes as a supplement to another antiepileptic treatment, or in monotherapy, for the treatment of sleep apnea, and for neuroprotection.

Accordingly, the subject of the present invention is also pharmaceutical compositions containing an effective dose of at least one compound according to the invention, in the form of a pharmaceutically acceptable base or salt or solvate, and in the form of a mixture, where appropriate, with suitable excipients.

The said excipients are chosen according to the pharmaceutical dosage form and the desired mode of administration.

The pharmaceutical compositions according to the invention may thus be intended for oral, sublingual, subcutaneous, intramuscular, intravenous, topical, intratracheal, intranasal, transdermal, rectal or intraocular administration.

The unit forms for administration may be, for example, tablets, gelatin capsules, granules, powders, oral or injectable solutions or suspensions, patches or suppositories. For topical administration, it is possible to envisage ointments, lotions and collyria.

The said unit forms contain doses in order to allow a daily administration of 0.01 to 20 mg of active ingredient per kg of body weight, according to the galenic form.

To prepare tablets, there are added to the active ingredient, micronized or otherwise, a pharmaceutical vehicle which may be composed of diluents, such as for example lactose, microcrystalline cellulose, starch, and formulation adjuvants such as binders, (polyvinylpyrrolidone, hydroxypropylmethylcellulose, and the like), flow-enhancing agents such as silica, lubricants such as magnesium stearate, stearic acid, glyceryl tribehenate, sodium stearylfumarate. Wetting agents or surfactants, such as sodium lauryl sulfate, may also be added.

The techniques for production may be direct compression, dry granulation, wet granulation or hot-melt.

The tablets may be uncoated, coated, for example with sucrose, or coated with various polymers or other appropriate materials. They may be designed to allow rapid, delayed or prolonged release of the active ingredient by virtue of polymer matrices or specific polymers used in the coating.

To prepare gelatin capsules, the active ingredient is mixed with dry (simple mixture, dry or wet granulation, or hot-melt), liquid or semisolid pharmaceutical vehicles.

The gelatin capsules may be hard or soft, film-coated or otherwise, so as to have rapid, prolonged or delayed activity (for example for an enteric form).

A composition in syrup or elixir form or for administration in the form of drops may contain the active ingredient together with a sweetener, preferably calorie-free, methylparaben or propylparaben as antiseptic, a flavor modifier and a coloring agent.

The water-dispersible powder and granules may contain the active ingredient in the form of a mixture with dispersing agents or wetting agents, or dispersants such as polyvinylpyrrolidone, and with sweeteners and flavor corrigents.

For rectal administration, suppositories are used which are prepared with binders which melt at rectal temperature, for example cocoa butter or polyethylene glycols.

For parenteral administration, there are used aqueous suspensions, isotonic saline solutions or sterile solutions for injection containing pharmacologically compatible dispersing agents and/or wetting agents, for example propylene glycol or butylene glycol.

The active ingredient may also be formulated in the form of microcapsules, optionally with one or more carriers or additives, or alternatively with a polymer matrix or with a cyclodextrin (patches, prolonged release forms).

The topical compositions according to the invention comprise a medium compatible with the skin. They may be provided in particular in the form of aqueous, alcoholic or aqueous-alcoholic solutions, gels, water-in-oil or oil-in-water emulsions having the appearance of a cream or of a gel, microemulsions, aerosols, or alternatively in the form of vesicular dispersions containing ionic and/or nonionic lipids. These galenic forms are prepared according to the customary methods in the fields considered.

Finally, the pharmaceutical compositions according to the invention may contain, apart from a compound of general formula (I), other active ingredients which may be useful in the treatment of the disorders and diseases indicated above.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A method of treating a disease selected from the group consisting of dementia, psychoses schizophrenia, acute or chronic extrapyramidal symptoms induced by neuroleptics, anxiety, panic attack, phobia, obsessive-compulsive disorder, depression, disorder due to alcohol abuse or withdrawal from alcohol, migraine, painful muscular contractures in rheumatology or acute spinal pathology, rebellious algia, Parkinson's disease, epilepsy, and sleep apnea in a patient comprising administering to said patient a therapeutically effective amount of a compound, in the form of a pure optical isomer (1S,2S) or in the form of a threo diastereoisomer, optionally in combination with a pharmaceutical excipient, wherein said compound is corresponding to general formula (1):

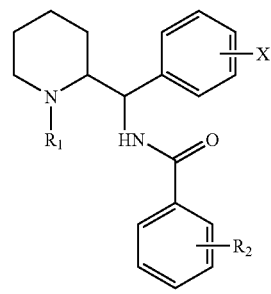

(I)

wherein $R_1$ is either a hydrogen atom, or a linear or branched ($C_1$-$C_7$)alkyl group optionally substituted with one or more fluorine atoms, or a ($C_3$-$C_7$)cycloalkyl($C_1$-$C_3$)alkyl group, or a phenyl($C_1$-$C_3$)alkyl group optionally substituted with one or two methoxy groups, or a ($C_2$-$C_4$) alkenyl group, or a ($C_2$-$C_4$)alkynyl group, X is a hydrogen atom or one or more substituents chosen from halogen atoms and trifluoromnethyl, linear or branched ($C_1$-$C_4$)alkyl and ($C_1$-$C_4$)alkoxy groups, $R_2$ is one or more substituents chosen from halogen atoms; and said compound in the form of a free base or of an addition salt with an acid.

2. The method as set forth in claim 1, wherein said compound is a glyt1 transporter inhibitor.

3. The method as set forth in claim 1, wherein said compound has the configuration (1S,2S), with $R_2$ representing one or more halogen atoms.

4. The method as set forth in claim 3, wherein said compound is a glyt1 transporter inhibitor.

5. The method as set forth in claim 4, wherein said disease is dementia.

6. The method as set forth in claim 4, wherein said disease is psychoses.

7. The method as set forth in claim 4, wherein said disease is schizophrenia.

8. The method as set forth in claim 7, wherein said schizophrenia is either deficient form or productive form.

9. The method as set forth in claim 4, wherein said disease is acute or chronic extrapyramidal symptoms induced by neuroleptics.

10. The method as set forth in claim 4, wherein said disease is anxiety.

11. The method as set forth in claim 4, wherein said disease is panic attack.

12. The method as set forth in claim 4, wherein said disease is phobia.

13. The method as set forth in claim 4, wherein said disease is obsessive-compulsive disorder.

14. The method as set forth in claim 4, wherein said disease is depression.

15. The method as set forth in claim 14, wherein said depression is psychotic depression.

16. The method as set forth in claim 4, wherein said disease is due to alcohol abuse or withdrawal from alcohol, and migraine.

* * * * *

UNITED STATES PATENT AND TRADEMARK OFFICE
CERTIFICATE OF CORRECTION

PATENT NO. : 7,951,821 B2
APPLICATION NO. : 11/680782
DATED : May 31, 2011
INVENTOR(S) : Gihad Dargazanli et al.

Page 1 of 1

It is certified that error appears in the above-identified patent and that said Letters Patent is hereby corrected as shown below:

In column 1, line 52, delete "(C2-C$_4$)" and insert -- (C$_2$-C$_4$) --, therefor.

In column 2, line 60, delete "R," and insert -- R$_1$ --, therefor.

In column 5, line 64, delete "R," and insert -- R$_1$ --, therefor.

In column 6, line 66, delete "N -" and insert -- N- --, therefor.

In column 7, line 66, delete "0°0C.," and insert -- 0°C., --, therefor.

In column 8, line 39, delete "+66.30" and insert -- +66.3° --, therefor.

In column 9, line 38, delete "ylpiperidin -2" and insert -- ylpiperidin-2 --, therefor.

In column 10, line 60, delete "+38.40" and insert -- +38.4° --, therefor.

In column 12, line 42, delete "three" and insert -- threo --, therefor.

In column 15, line 25, delete "CH$_3$" and insert -- H --, therefor.

In column 15, line 45, delete "[$^1$4C]" and insert -- [$^{14}$C] --, therefor.

In column 20, line 23, in claim 1, delete "trifluoromnethyl," and insert -- trifluoromethyl, --, therefor.

Signed and Sealed this
Twenty-fifth Day of October, 2011

David J. Kappos
*Director of the United States Patent and Trademark Office*